(12) United States Patent
Peters

(10) Patent No.: US 9,645,162 B2
(45) Date of Patent: May 9, 2017

(54) AUTOMATED ASSAY FLUID DISPENSING

(71) Applicant: HEWLETT-PACKARD DEVELOPMENT COMPANY, L.P., Houston, TX (US)

(72) Inventor: Kevin F Peters, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 476 days.

(21) Appl. No.: 13/754,708

(22) Filed: Jan. 30, 2013

(65) Prior Publication Data

US 2013/0143328 A1 Jun. 6, 2013

Related U.S. Application Data

(63) Continuation-in-part of application No. 12/870,546, filed on Aug. 27, 2010, now Pat. No. 9,433,939.

(51) Int. Cl.
*G01N 21/00* (2006.01)
*G01N 35/10* (2006.01)
(Continued)

(52) U.S. Cl.
CPC ........ *G01N 35/1002* (2013.01); *B01L 3/0268* (2013.01); *B01L 3/545* (2013.01); *G01N 35/0092* (2013.01); *B01L 2200/04* (2013.01); *B01L 2200/061* (2013.01); *B01L 2200/0642* (2013.01); *B01L 2200/143* (2013.01); *B01L 2200/16* (2013.01); *B01L 2300/021* (2013.01); *B01L 2300/022* (2013.01); *B01L 2400/02* (2013.01); *G01N 35/1016* (2013.01); *G01N 2021/513* (2013.01); *G01N 2035/00891* (2013.01); *Y10T 436/11* (2015.01)

(58) Field of Classification Search
CPC G01N 35/1002; B01L 3/0268; B01L 2200/04
See application file for complete search history.

(56) References Cited

U.S. PATENT DOCUMENTS 4,940,998 A 7/1990 Asakawa
5,877,580 A 3/1999 Swierkowski
(Continued)

FOREIGN PATENT DOCUMENTS

| CH | EP 1859870 A1 * 11/2007 | ............ B01L 3/021 |
|---|---|---|
| JP | 8201394 | 8/1996 |
| WO | WO-2009070540 | 6/2009 |

*Primary Examiner* — P. Kathryn Wright
(74) *Attorney, Agent, or Firm* — Clifton L. Anderson

(57) ABSTRACT

An automated assay-fluid dispensing system includes a database that associates assay protocols with assay procedures, the procedures including a first assay procedure specifying dissimilar first and second channel procedures for driving first and second channels of a fluid-dispenser cassette. The system includes a controller with a procedure selector to select or to assist a human to select an assay procedure from the database to be executed in an assay run. The controller also includes a cassette driver to drive the cassette to dispense fluids automatically to multiple sites during the assay run so that fluids in the first and second channels are dispensed in accordance with the dissimilar first and second channel procedures. The system includes a cassette interface to engage the cassette so that the controller can drive it to implement the assay run.

13 Claims, 3 Drawing Sheets

(51) Int. Cl.
  *B01L 3/02* (2006.01)
  *G01N 35/00* (2006.01)
  *B01L 3/00* (2006.01)
  *G01N 21/51* (2006.01)

(56) References Cited

U.S. PATENT DOCUMENTS

| | | |
|---|---|---|
| 5,940,099 A | 8/1999 | Karlinski |
| 6,068,367 A | 5/2000 | Fabbri |
| 6,431,673 B1 * | 8/2002 | Heim et al. ............... 347/9 |
| 6,460,964 B2 | 10/2002 | Osborne |
| 6,710,878 B1 | 3/2004 | Dean et al. |
| 7,138,254 B2 | 11/2006 | Jovanovich et al. |
| 7,707,964 B2 | 5/2010 | Childers |
| 7,819,847 B2 | 10/2010 | Vitello et al. |
| 8,215,262 B2 | 7/2012 | Ishikawa et al. |
| 2002/0089561 A1 | 7/2002 | Weitzel et al. |
| 2002/0121529 A1 | 9/2002 | Hoummady |
| 2002/0140770 A1 | 10/2002 | Silverbrook et al. |
| 2002/0140776 A1 | 10/2002 | Silverbrook et al. |
| 2002/0140777 A1 | 10/2002 | Silverbrook et al. |
| 2002/0191049 A1 | 12/2002 | Silverbrook |
| 2003/0086828 A1 * | 5/2003 | Chiou et al. ............... 422/100 |
| 2003/0137554 A1 | 7/2003 | Silverbrook et al. |
| 2004/0036726 A1 | 2/2004 | Zach |
| 2004/0254527 A1 | 12/2004 | Vitello et al. |
| 2005/0214775 A1 * | 9/2005 | Adaskin ............... B01J 19/0046 435/6.19 |
| 2006/0139405 A1 | 6/2006 | Nellen |
| 2007/0111322 A1 | 5/2007 | Yang |
| 2008/0170089 A1 | 7/2008 | Albertalli et al. |
| 2009/0088336 A1 * | 4/2009 | Burd ............... B01J 19/0046 506/9 |
| 2009/0124015 A1 * | 5/2009 | Dussi et al. ............... 436/43 |
| 2009/0244151 A1 | 10/2009 | Hendricks et al. |
| 2010/0265287 A1 | 10/2010 | Govyadinov et al. |
| 2012/0051984 A1 | 3/2012 | Dudenhoefer et al. |

* cited by examiner

AUTOMATED ASSAY FLUID DISPENSING

This is a continuation-in-part of copending U.S. patent application Ser. No. 12/870,546, filed 2010 Aug. 27, now published as U.S. Patent Publication 2012/0051984 A1.

BACKGROUND

An "assay run" is an investigative (analytic) event, e.g., in laboratory medicine, pharmacology, analytical chemistry, environmental biology, or molecular biology, for qualitatively assessing or quantitatively measuring the presence, amount, or the functional activity of a sample, which can be a drug, biochemical substance, or a cell in an organism or an organic sample. The assay run usually aims to measure an intensive property of the sample and express it in the relevant measurement unit (e.g. molarity, density, functional activity in enzyme international units, degree of some effect in comparison to a standard, etc.) An assay can involve reacting a sample with certain reagents. An assay run is typically an instance of an assay procedure conforming to a (possibly standardized) assay protocol. An assay protocol commonly involves a set of reagent and/or sample fluids being dispensed in specific amounts to assay reaction sites, as well, sometimes, as additional steps such as mixing, separation, heating or cooling, incubation, and eventually one or more read-outs. The reproducibility and run-to-run comparability of an assay depends on the reproduction of its protocol.

Automated assay fluid dispensing systems can dispense assay fluids, e.g., samples and reagents, in a precise, controlled fashion to multiple reaction sites in a short time; for example, a carefully formulated mixture of several reagents, including a target species of interest, can be carefully formulated at multiple reaction sites for the testing of a set of test sample reagents at multiple concentrations. This allows many reactions to proceed contemporaneously. The automation reduces user effort and user-caused variability, while the concurrency further reduces the time to complete a complex assay.

BRIEF DESCRIPTION OF THE DRAWINGS

The following figures represent examples and not the invention itself.

DETAILED DESCRIPTION

Figure 1:
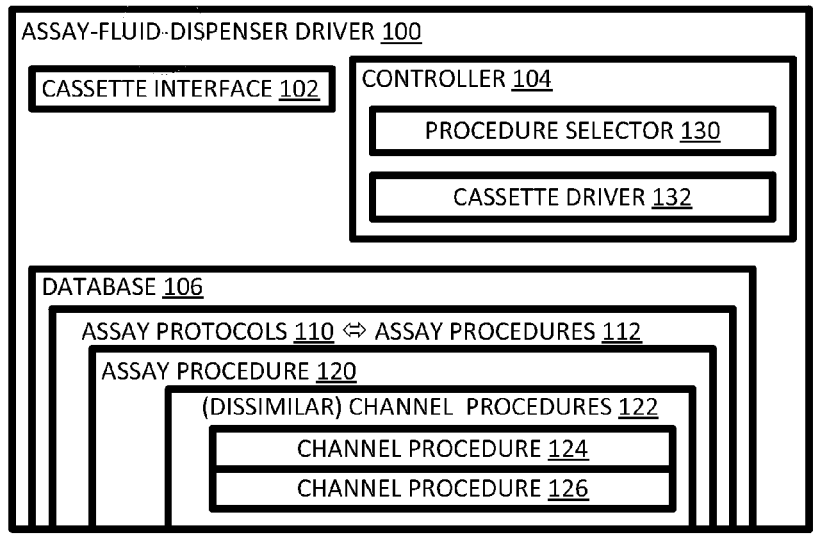
FIG. 1 is a schematic diagram of an automated assay-fluid-dispenser driver.
Figure 2:
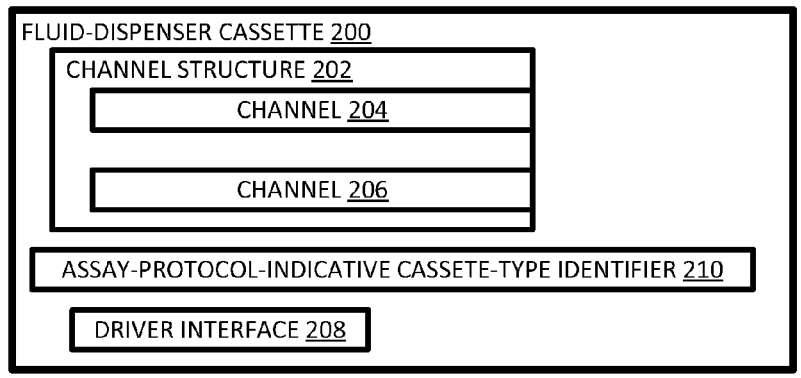
FIG. 2 is a schematic diagram of an assay-protocol-specific multi-channel fluid-dispenser cassette.

Automated fluid dispensing systems are available to dispense one or more assay fluids (e.g., analyte, reagents) to plural reaction sites at a time. Some automated fluid dispensing systems employ a fluid-dispenser driver that uses interchangeable cassettes; the cassettes can contain assay fluids and can be controlled so that they deposit assay fluids onto reaction sites. For example, a reaction medium can be moved relative to the cassette so that, over (a relatively short) time, an assay fluid can be deposited (in the same or varying amounts) at different reaction sites of the reaction medium. The reaction medium can be, for example, a microtitre plate in which an array of reaction wells is defined, a tissue sample, a chip with integrated microfluidics, or a glass slide.

Multi-channel cassettes can be used so that multiple fluids can be dispensed contemporaneously. For example, multiple samples can be deposited at respective reaction sites in parallel or quickly in serial in order to reduce the time required to titrate a plurality of samples. Herein, "cassette" refers to a user-replaceable component of a dispenser system, through which one or more fluids flow through, respectively, one or more fluid channels before being dispensed from the dispensing system.

In a typical prefabricated multi-channel fluid-dispenser cassette (e.g., the Hewlett-Packard T-8 cassette for use with the Hewlett-Packard D300 Digital Dispenser), the channels are nominally identical, as is appropriate, for example, when titrating a set of samples with similar fluid properties. However, many assay protocols call for the use of different assay fluids with very different fluid properties or handling requirements. For example, some assay fluids are more viscous than others, some assay fluids may be required in large volume, while others, e.g., potent samples, may require small precisely controlled amounts, and some assay fluids may require specific conditions, e.g., conduit coatings and temperature control. Moreover, many assay protocols stipulate the exact sequence and timing of the fluid handling and other non-dispensing steps, such as mixing or reading.

Some users have addressed the problem of handling dissimilar fluids and assay requirements by forming custom assemblies of dispense-heads with fluid-specific characteristics. A user may then develop a custom assay procedure based on the custom dispense-head assembly. While it achieves greater flexibility, this custom and modular approach does so at the cost of a loss of automation, standardization, and reproducibility among users with similar yet different procedures. Examples disclosed herein can achieve flexibility without sacrificing loss of automation, standardization, and reproducibility.

In accordance with some examples described herein, an assay-fluid dispensing system can include an assay-fluid-dispenser driver to control interchangeable assay-protocol-specific multi-channel fluid-dispenser cassettes. The driver can include a database associating protocols with automated assay procedures implementable by the fluid dispensing system. The procedures can specify that different channels of a cassette are to be driven dissimilarly according to the characteristics and protocol requirements for the fluids to be dispensed from those channels.

The cassette may have a corresponding "cassette type", wherein the cassette type defines a class of nominally identical cassettes. The cassette may include a cassette-type identifier that indicates a set of one or more assay protocols which the cassette may be used to implement. The identifier may be read, e.g., by a human and/or the dispenser driver, to identify the protocol and, for each channel, the assay fluid to be dispensed. An automated dispenser driver can use this indication to select an assay procedure and/or determine what choices to present to an operator. Some cassettes may include dissimilar channels to accommodate differing fluid volumes, precisions, and characteristics without imposing requirements for dispense head assembly on a user. The dispenser driver can then select and help a human operator to select an automated assay procedure to be implemented according to an indicated assay protocol. For further convenience, assay kits can be manufactured and sold/purchased or otherwise provided that they include a prefabricated assay-protocol-specific fluid-dispenser cassette along with the reagents to be used in the assay.

In some examples, preparation for an assay run simply involves: 1) selecting a multi-channel cassette of the appropriate type; 2) ensuring, for each channel, that the indicated fluid is provided; 3) installing the cassette and reaction medium into the driver. In some examples, the assay run may be automated upon installation of the cassette. In other examples, a (human) operator may be allowed to select among alternative assay protocols or assay protocol variations, or to set or modify assay procedure parameters before automated dispensing begins.

An assay-fluid-dispenser driver 100, shown in FIG. 1, includes a cassette interface 102, a controller 104, and a database 106. Database 106 associates standardized assay protocols 110 with assay procedures 112. At least one assay procedure 120 includes channel procedures 122, including dissimilar channel procedures 124 and 126 for driving different channels of a cassette dissimilarly, e.g., to accommodate dissimilar channels, fluid characteristics, or assay requirements. Controller 104 includes a procedure selector 130 to select an assay procedure represented in database 106. Controller 104 includes a cassette driver 132 to communicate with a cassette via cassette interface 102 so that the cassette dispenses fluids according to a selected assay procedure.

A prefabricated assay-protocol-specific multi-channel fluid-dispenser cassette 200 includes a channel structure 202, including a channel 204 and a channel 206. Fluid-dispenser cassette 200 also includes a drive interface 208 to interface with an automated assay-fluid-dispenser drive to constitute an automated assay-fluid dispensing system. Cassette 200 also includes a cassette-type identifier 210 indicative of an assay protocol.

Figure 3:
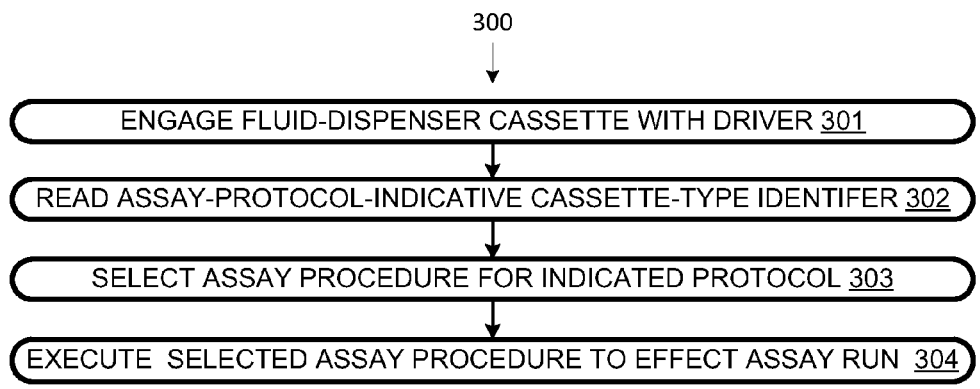
FIG. 3 is a flow chart of an assay process using an automated fluid dispensing system.

An assay process 300 is flow charted in FIG. 3. At 301, a fluid-dispenser cassette having a protocol-specific identifier is engaged with a dispenser driver. At 302, a protocol-specific identifier is read from a fluid-dispenser cassette. At 303, an assay procedure is determined based at least in part on the assay-protocol-indicative cassette-type identifier. At 304, the assay procedure is executed to yield an assay run. In alternative examples, the order of some of the actions is changed; for example, the protocol-specific identifier may be read before the cassette is engaged.

Herein, "channel" refers to a structure through which a fluid can flow on its way to being dispensed. A channel can include a "conduit" to physically constrain and guide fluid flow. A channel can include one or more drive elements to drive fluid along the channel and to eject the fluid from the channel as it is dispensed. A channel can include a reservoir for a fluid and/or an interface to a fluid reservoir. A channel can include an outlet (schematically shown as "O" in FIG. 4), such as one or more nozzles, from which the fluid is dispensed as it is ejected from the channel. A channel may also include other elements to condition fluid in a channel, e.g., heaters (schematically shown as "H" in FIG. 4) to pre-heat a fluid to a desired temperature; filters to isolate particulate larger than a prescribed size; and other fluid conditioning devices such as mixers, separators, concentrators, and incubators that are well known to those practiced in the arts of microfluidics and chemical engineering. A "multi-channel cassette" is a cassette that includes two or more fluid channels, e.g., for contemporaneous dispensing of at least two fluids.

Herein, a "type identifier" is a human-readable and/or machine-readable entity that identifies a class of plural objects to which the object being identified belongs. "Type", herein, refers to a class of plural instances rather than the instances themselves; thus, herein, a unique instance does not have a type. Typically, a model number would qualify as a type identifier, while a serial number for a particular instance of a model would not unless it contains some elements unique to its type. A "cassette-type identifier" is an identifier that identifies a type of cassette.

A cassette-type identifier that indicates an assay protocol or set of assay protocols for which the cassettes of the same type are to be used qualifies, herein, as "assay-protocol-indicative". For example, a label stating "this model cassette is for assay protocol A" in a human and/or machine-readable format (e.g., a bar code or QR code with text, a digital electronic or RFID code, a specific mechanical keying shape) qualifies as "assay-protocol-indicative". However, even a simple model number can be "assay-protocol-indicative".

Herein, a cassette is "prefabricated" if assembly is complete upon manufacture. If the cassette is sold, assembly must be complete at the time of sale. A cassette assembled by a user after manufacture and sale is not "prefabricated". Correspondingly, "factory-introduced" denotes introduction during or upon manufacture, as opposed to introduction by a user, e.g., after purchase.

Figure 4:
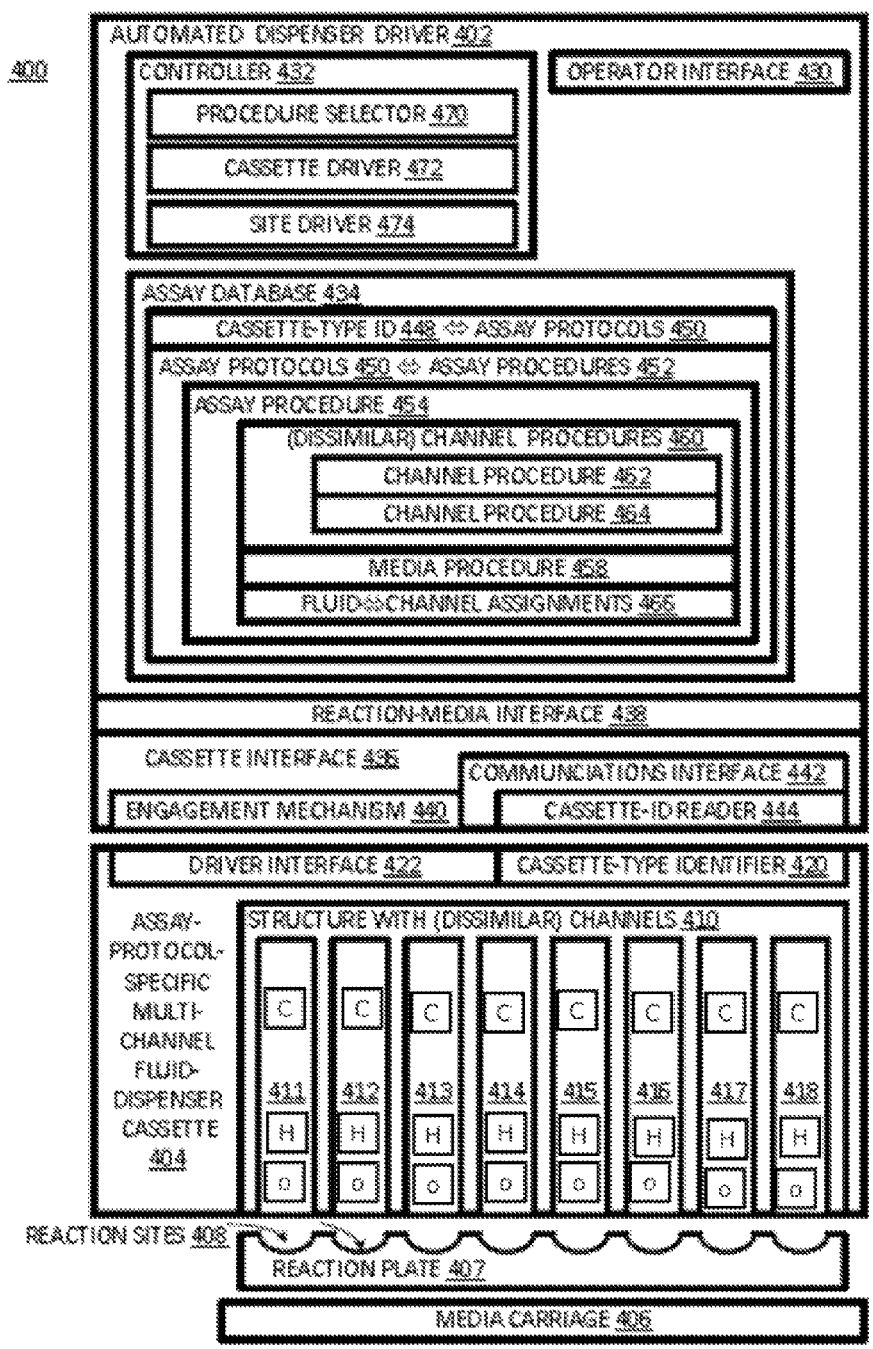
FIG. 4 is a schematic diagram of an automated fluid dispensing system.

An automated assay-fluid dispensing system 400, shown in FIG. 4, may include a dispenser driver 402, a fluid-dispenser cassette 404, and a media carriage 406. Media carriage 406 is shown in FIG. 4 carrying a reaction plate 407. Fluid-dispenser cassette 404 and reaction plate 407 may be considered user-replaceable components of dispensing system 400. Reaction plate 407 may have defined in it a set of reaction sites 408, such as in a two-dimensional array, for example: a microtitre plate. Each well is a site into which assay fluids may be dispensed so that they may react with each other and/or with the media.

Fluid-dispenser cassette 404 includes multiple channels 410. In this specific example, there are eight channels 411, 412, 413, 414, 415, 416, 417, and 418. Each channel can hold and dispense a respective assay fluid. The channels may hold a like number of different reagents, or there may be some duplication among the channels. At least channels 411 and 412, for example, may be dissimilar.

Fluid-dispenser cassette 404 includes a manufacturer-provided cassette-type identifier 420 indicative of a set of one or more assay protocols. For example, the identifier can be a label with a machine-readable bar code along with text specifying a particular assay protocol. An indication of which assay fluids go in which channels may be included on the identifier, which can be monolithic or distributed, e.g., over the respective channels. The channels may include reservoirs for the respective fluids or have interfaces for fluid communications with reservoirs holding respective assay fluids. Conveniently, the cassette, and one, some, or all reagents for an assay may be manufactured and sold/purchased or otherwise provided/obtained together as an assay kit.

Dispenser cassette 404 includes a driver interface 422 that provides for mechanical engagement with dispenser driver 402. In addition, driver interface 422 provides for communications between driver 402 and dispense head 404. The communications can include commands that determine when and how much fluid is dispensed from a particular channel at a particular time. Furthermore, driver interface 422 allows driver 402 to supply power to dispense head, e.g., to heat resistors used to eject fluid from a channel. In some examples, driver interface 422 can convey information from the cassette 404 back to the driver 402, such as temperature and functionality performance measures.

Dispenser driver 402 includes a user (e.g., operator) interface 430, a controller 432, an assay-method database 434, a cassette interface 436, and a reaction-media interface 438. Cassette interface 436 includes an engagement mechanism 440 and a communications interface 442, which includes a cassette-ID reader 444. Engagement mechanism 440 is to engage a dispense head when the dispense head is installed into or engaged with driver 402. Communications interface 442 is to provide for communications of commands and information between driver 402 and cassette 404. Cassette-ID reader 444 is to read cassette-type identifiers 420 from cassettes. Reaction-media interface 438 is to engage reaction media, e.g., reaction plate 407, so that each channel 411-418 can dispense its contents to different reaction sites as the reaction media is moved stepwise relative to cassette 404.

Assay database 434 can be in the form of non-transitory computer-readable media encoded with code defining the database structure and its contents. Assay database 434 associates cassette-type identities, e.g., as obtained from cassette-type identifier 420, with assay protocols 450. In an alternative database, cassette-type identifiers are associated directly with assay procedures. Assay database 434 also associates assay protocols 450 with assay procedures 452. Assay procedures 452 specify sequences of operations performable by automated assay system 400, including driver communication with channels, e.g., channels 411-418 of cassette 404. Note that assay database 434 can be updated to modify or replace the procedure associated with a protocol.

Database 434 associates with the protocol indicated by cassette-type identifier 420 an assay procedure 454. Other cassettes of the same type indicate the same protocol and thus will call up the same procedure. Cassettes of different types may have different type identifiers that will indicate different protocols associated with different procedures. Some cassette types may be suited to more than one protocol; in such cases, the type identifier may indicate a set of compatible protocols; these compatible protocols may be associated with other procedures.

Assay procedure 454 may include channel procedures 460. Typically, the number of channel procedures can equal the number of fluid channels 410 in the cassette used in the procedure. Among the channel procedures 460 of assay procedure 454, channel procedures 462 and 464 are dissimilar. For some assay procedures, all channel procedures are similar; for other assay procedures, all channel procedures may be unique (i.e., each channel procedures is dissimilar to each other channel procedure of the assay procedure); for still other assay procedures, some pairs of channel procedures are dissimilar and some pairs are similar. Depending on the example, similar fluid channels may be driven similarly or dissimilarly, and dissimilar fluid channels may be driven similarly or dissimilarly.

In addition to specifying channel procedures 460, assay procedure 454 can specify, as part of its setup, fluid-to-channel assignments 466; this is which assay fluids are to be dispensed from which cassette channels. Also, assay procedure 454 can specify an assay-media procedure 458, dictating how an assay media is to be moved relative to a fluid-dispenser cassette so that each fluid can be dispensed to different reaction sites.

Controller 432 is programmed hardware. Controller 432 includes a procedure selector 470, a cassette driver 472, and a site driver 474. Cassette driver 472 can read identification information from a cassette-type identifier. Procedure selector 470 can use the identification information to look up a protocol and an associated procedure from database 434. During an assay run, controller 432 causes cassette driver 472 and site driver 474 to coordinate the dispensing of fluids from a cassette with the stepped position of a reaction medium so that at the desired time the desired amount of fluid is dispensed to each reaction site. Precise dispense times can be critical to procedures calling for specific reaction start and stop times to establish desired reaction durations and to ensure proper ordering of procedure steps.

Some cassette-type identifiers may indicate a set of more than one assay protocol. For such identifiers, procedure selector 470 may communicate with a user via operator interface 430 so that the user can indicate which protocol of the plural indicated pluralities is to be executed. Some procedures may afford user choices. For such procedures, procedure selector 470 can communicate with a user via operator interface 430 to allow the user to select among procedure variations or to set or adjust procedure parameters. On the other hand, if the assay procedure is sufficiently specific, dispensing system 400 can then carry out an assay procedure automatically without further operator input.

From an enterprise perspective, it is implicit in the existence of a cassette-type identifier that there are other cassettes of the same type and that there are cassettes of different types for different assay protocols. Each fluid-dispenser cassette can then be optimized for its respective assay protocol.

As part of this optimization, some cassettes, e.g., cassette 404, can have dissimilar channel characteristics for different assay fluids (e.g., reagents and analytes). These fluids may be quite dissimilar from another in their solvent, solute, concentration, formulation, total volume, storage temperature, dispensed temperature, potency, value, etc. The assay fluids may also differ in ways that have specific meaning to the dispensing and assay protocol, e.g.: required volume, viscosity, warming requirement, temperature limits, heat of vaporization and inkjet turn-on-energy, priming ability, fragility, preferred rate of dispensing, order of dispensing, adsorption potential, drop placement, and particulate or microsphere distribution. An assay fluid may also be a sample that is not commercially provided but rather is provided by an investigator/experimentalist (such as blood, plasma, serum, tissue extracts, cell lysates, primer, reagents, indicators, antibodies, and concentrated molecules of DNA, RNA, enzymes, proteins, effectors, cofactors, small molecules, drug compounds, etc.).

Accordingly, the number and characteristics of channels in a multi-channel fluid-dispenser cassette can be protocol or procedure-specific. Channels may differ in a number of ways that are known in various dispensing arts including inkjet printing. Depending on the drive technology, the following are examples of parameters along which channels may be dissimilar; e.g.: maximum or minimum fluid load volume, channel materials, surface preparation, or geometry; nozzle, ejection chamber and microchannel geometry, particle management architecture, thermal inkjet or piezo-electric firing pulse energy, frequency, amplitude, duration, hydraulic or pneumatic pressure duration and amplitude. Such characteristics are well known to those practices in the arts of printing, dispensing, inkjet, microfluidics, and assay sciences.

For example, a first channel may provide for relatively high throughput for a first reagent to be dispensed in relatively high volumes, while another channel of the same cassette provides for more precise control of an analyte; precise control can minimize waste of a precious sample or over-dosing of a potent sample. A third channel can have a resistive heating element for a reagent that needs to be warmed or maintained at a particular temperature. A fourth channel may have a particular coating (schematically shown as "C" in FIG. 4) for chemical compatibility with a reagent, such as to promote priming or to avoid solute sorptive loss.

A cassette-type identifier can be a single item, e.g., a label, or multiple items. For example, multiple identifier elements can be used, e.g., to identify the assay fluids for each channel. Depending on the example, the identifiers can be human readable and/or machine readable. The identifiers can be mechanical, optical, magnetic, electronic, etc. In some examples, an identifier may also bear information about the dispensing and assay method. For example, timing, volumes, preheating, reaction media type and format, experimental layouts, and other design considerations may be specified. In other examples, such information may be discerned separately upon identification of the cassette.

Figure 5:
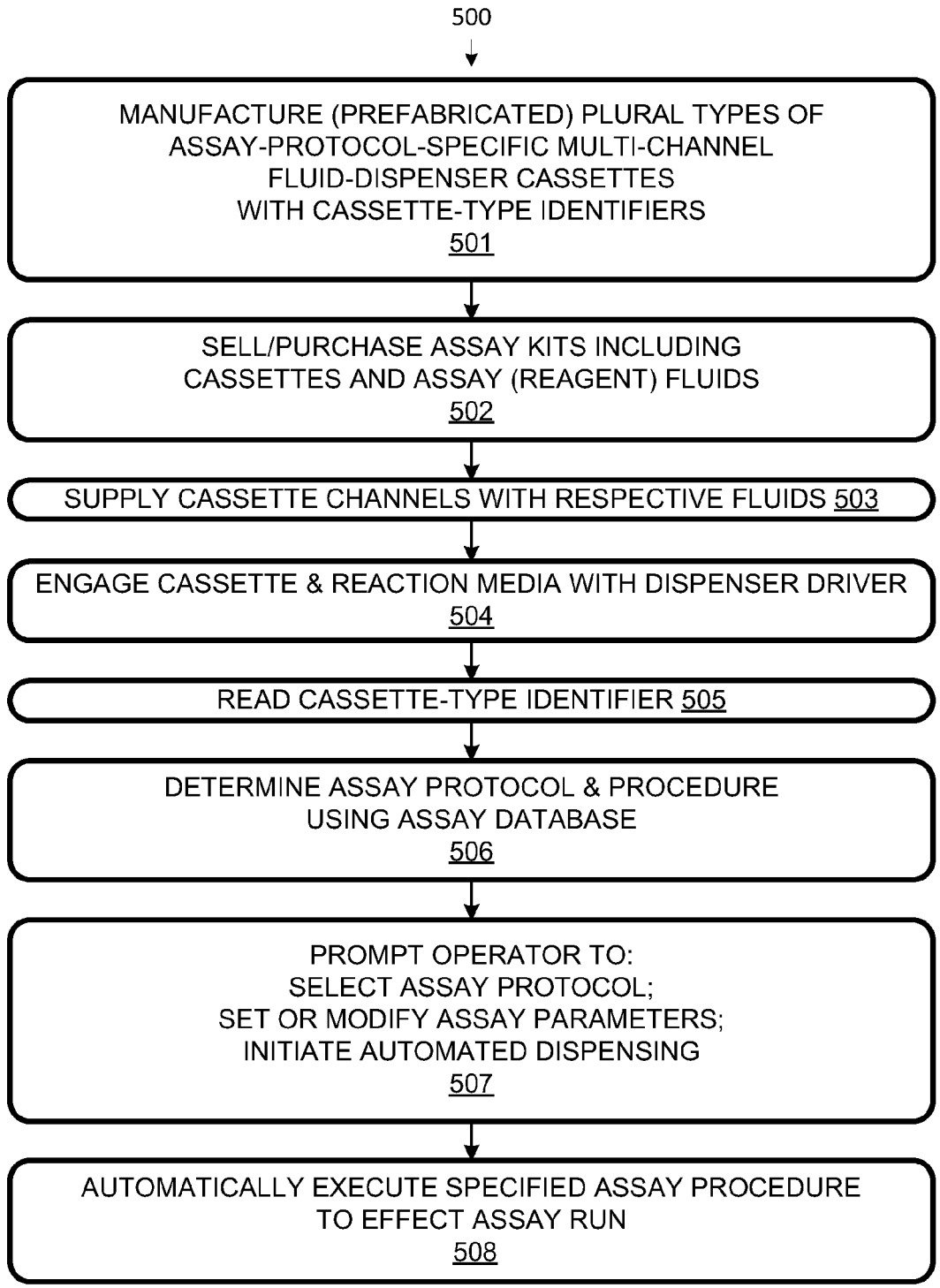
FIG. 5 is a flow chart of a process from manufacture through use of an assay-protocol-specific multi-channel fluid-dispenser cassette.

In a process 500, flow charted in FIG. 5, at 501, prefabricated assay-protocol-specific multi-channel fluid-dispenser cassettes are manufactured (by one or more manufacturers). That is, there are more than one cassette types manufactured and more than one cassette per cassette type. Each cassette is manufactured with a cassette-type identifier indicative of a corresponding set of one or more assay protocols. The identifier may be monolithic or distributed, e.g., each of the channels may include an identifier element to indicate what assay fluid is to be dispensed using that channel.

At 502, assay kits are factory packaged and sold/purchased. Each assay kit includes a cassette and some or all of the assay fluids, e.g., reagents for an assay type. Typically, samples (analytes) would not be provided in an assay kit; an exception would be a test sample standard, having known reactivity in the assay. Depending on the example, some or all of the reagents or components thereof may be contained in one or more channels of a prefabricated (as manufactured) cassette, in which case those moeities are contained during sale/purchase. After purchase, an operator or investigator can introduce samples, reagents, reagent components, and or other assay fluids, into one or more channels at 503.

At 504, a cassette is installed in the dispenser driver. In some scenarios, one or more reservoirs or other fluid sources may be connected to a dispenser cassette after installation. At 505, an assay protocol-indicative cassette-type identifier is read. In an alternative example, the identifier is read, e.g., by a user, before the cassette is engaged with the driver. The user can then enter into the driver information to determine which procedure to execute. In another alternative, the procedure is pre-selected and the cassette is purchased/selected to match the selected procedure.

At 506, an assay protocol and associated procedure are determined based on the information obtained from the cassette-type identifier. In some examples, actions 505 and 506 are performed automatically by the dispenser system. In other examples, one or both of actions 505 and 506 are performed by a user.

At 507, the dispenser system prompts or otherwise allows an operator to make selections. If more than one assay protocol is determined at 506, the operator may select the assay protocol desired. If a determined or selected assay procedure has parameters that can be set or modified, this can be done at 507. In some examples, an operator can instruct the dispensing system when to initiate execution of the specified assay procedure. This execution is automated and occurs at 508, affecting an assay run.

Examples herein provide for customization of dispensing and dispensing attributes for specific assay protocols and specific fluids used in those protocols. Dissimilar dispensing functions for different assay fluids specified for a single assay protocol can be integrated into a single multi-channel fluid-dispenser cassette. The volumes of some fluids can be precisely controlled, minimizing waste of precious reagents and dispensing the smallest amount of potent samples, while other fluids can be dispensed contemporaneously at high volumes. This in turn allows for higher overall performance.

Cassette-type identifications indicative of an assay protocol simplify the task of the operator, reducing the skill levels to carry out an assay. Preparation effort is eased, mistakes and errors are reduced. Further simplification can be achieve by manufacturing, marketing, and purchasing assay kits, each including the assay-method-specific dispense head and the assay fluids to be dispensed using the fluid-dispenser cassette.

Herein, a "system" is a set of interacting non-transitory tangible elements, wherein the elements can be, by way of example and not of limitation, mechanical components, electrical elements, atoms, physical encodings of instructions, and process actions. Herein, "process" refers to a sequence of actions resulting in or involving a physical transformation.

Herein, a "fluid-dispenser cassette" is an object designed to dispense fluids. Herein, a "cassette type" is a class of plural nominally identical cassettes. For example, cassette A and cassette B are of the same type, and if, in cassette A, channels 1 and 2 are dissimilar in a particular way, then channels 1 and 2 of cassette B are dissimilar in the same way.

Herein, "similar" and "dissimilar" are to be interpreted as referring to characteristics that are meaningful in an assay context. The similarities and dissimilarities referred to as such herein are assay-procedure and fluid specific. For example, dissimilar channels of a cassette may bear the same fluid moiety, but the channels may be driven dissimilarly; e.g., to dispense gross and fine amounts of the fluid using the different channels. Examples of parameters that may be varied to yield dissimilar channels include nozzle or channel dimensions, channel fluid supply volume, droplet ejection control parameters, filter dimensions, and material of channel surface contacting fluid, and other parameters.

Herein, an "assay run" is an event involving reactions among fluids for purposes of chemical analysis. Herein, an "event", is a time-bounded occurrence. Herein, an "assay protocol" is a standardized specification for a class of assay runs. Herein, an "assay procedure" is a repeatable sequence of operations for implementing an assay protocol such that execution of the sequence results in an assay run conforming to the assay protocol. There can be alternative assay procedures for implementing an assay protocol. For example, an automated assay fluid dispensing system can employ a proprietary assay procedure conforming to a standardized assay protocol. An assay run is an instance of an assay procedure and of the assay protocol to which the assay procedure implements.

In this specification, related art is discussed for expository purposes. Related art labeled "prior art", if any, is admitted prior art. Related art not labeled "prior art" is not admitted prior art. The illustrated and other described embodiments, as well as modifications thereto and variations thereupon are within the scope of the following claims.

What is claimed is:

1. An assay-protocol-specific multi-channel fluid-dispenser cassette for an automated assay fluid dispensing system, the cassette comprising:
a structure with multiple fluid channels within the structure to contain and control respective assay fluids, each of the fluid channels having an outlet;
a driver interface carried by the structure and engageable with to engage a dispenser driver so that the dispenser driver can control the dispensing of fluids from the structure directly onto underlying reaction sites while each of the fluid channels remain as part of the structure;
an assay-protocol-indicative cassette-type identifier formed in or attached to the structure and indicative of different assay protocols for all of the multiple fluid channels, wherein the multiple fluid channels comprise:
a first channel having physical parameters to provide for a first throughput rate; and
a second channel having physical parameters to provide a second throughput rate less than the first throughput rate.

2. An assay-protocol-specific multi-channel fluid-dispenser cassette as recited in claim 1 wherein at least two of the fluid channels are dissimilar to accommodate different channel or assay specifications for the different respective assay fluids.

3. An assay-protocol-specific multi-channel fluid-dispenser cassette as recited in claim 1 wherein the identifier is human readable or is readable by the dispenser driver.

4. An assay-protocol-specific multi-channel fluid-dispenser cassette as recited in claim 1 further comprising a factory-introduced reagent or reagent component in one of the multiple channels.

5. An assay-protocol-specific multi-channel fluid-dispenser cassette as recited in claim 1 wherein the identifier indicates, for each channel, the assay fluid to be handled by that channel.

6. An assay-protocol-specific multi-channel fluid-dispenser cassette as recited in claim 2, wherein the multiple fluid channels are dissimilar with respect to at least one parameter selected from a group of parameters consisting of: maximum fluid load volume; minimum fluid load volume; channel materials; surface preparation; surface geometry; nozzle geometry; ejection chamber geometry; microchannel geometry; particle management architecture; thermal inkjet firing pulse energy; piezo-electric firing pulse energy, amplitude, duration; hydraulic pressure duration; hydraulic pressure amplitude; pneumatic pressure duration and pneumatic pressure amplitude.

7. An assay-protocol-specific multi-channel fluid-dispenser cassette as recited in claim 1, wherein the multiple fluid channels comprise a third channel having a resistive heating element to maintain fluid at a predetermined temperature.

8. An assay-protocol-specific multi-channel fluid-dispenser cassette as recited in claim 7, wherein the multiple fluid channels comprise a fourth channel having an internal reagent compatible coating.

9. The assay-protocol-specific multi-channel fluid-dispenser cassette as recited in claim 1, wherein the outlet comprise a nozzle and wherein each of the fluid channels further comprises an electrically resistive heater to eject fluid from the channel through the nozzle.

10. An assay-protocol-specific multi-channel fluid-dispenser cassette for an automated assay fluid dispensing system, the cassette comprising:
a structure with multiple fluid channels to contain and control respective assay fluids, wherein at least two of the fluid channels are dissimilar to accommodate different channel or assay specifications for different respective assay fluids, wherein the multiple fluid channels comprise:
a first channel having physical parameters to provide for a first throughput; and
a second channel having physical parameters to provide a precisely controlled second throughput less than the first throughput; and
a third channel having a resistive heating element to maintain fluid at a predetermined temperature; and
a driver interface to engage a dispenser driver so that the dispenser driver can control the dispensing of fluids from the structure;
an assay-protocol-indicative cassette-type identifier located in or attached to the structure and indicative of at least one assay protocol.

11. The assay-protocol-specific multi-channel fluid-dispenser cassette of claim 10, wherein the fluid channels are dissimilar with respect to at least one parameter selected from a group of parameters consisting of: maximum fluid load volume; minimum fluid load volume; channel materials; surface preparation; surface geometry; nozzle geometry; ejection chamber geometry; microchannel geometry; particle management architecture; thermal inkjet firing pulse energy; piezo-electric firing pulse energy, amplitude, duration; hydraulic pressure duration; hydraulic pressure amplitude; pneumatic pressure duration and pneumatic pressure amplitude.

12. The assay-protocol-specific multi-channel fluid-dispenser cassette of claim 10, wherein the multiple fluid channels comprise a fourth channel having an internal reagent compatible coating.

13. The assay-protocol-specific multi-channel fluid-dispenser cassette as recited in claim 10, wherein the multiple fluid channels comprise a fourth channel having an internal coating to promote priming or avoid solute sorptive loss.

* * * * *